United States Patent [19]

Slater

[11] Patent Number: 4,654,342

[45] Date of Patent: Mar. 31, 1987

[54] 6-(CYANOGUANIDINOPHENYL)PYRIDAZINONES AS CARDIAC STIMULANTS

[75] Inventor: Robert A. Slater, Letchworth, England

[73] Assignee: Smith Kline & French Laboratories Ltd., Welwyn Garden City, England

[21] Appl. No.: 690,911

[22] Filed: Jan. 14, 1985

[30] Foreign Application Priority Data

Jan. 13, 1984 [GB] United Kingdom ................. 8400863

[51] Int. Cl.$^4$ .................... C07D 237/04; A61K 31/50
[52] U.S. Cl. .................................... 514/247; 544/239; 560/19; 560/35; 562/439; 562/440; 562/433
[58] Field of Search .......................... 544/239; 514/247

[56] References Cited

U.S. PATENT DOCUMENTS 3,822,260  7/1974  Curran et al. ........................ 544/239

FOREIGN PATENT DOCUMENTS 30835    6/1981  European Pat. Off. .
0084250  7/1983  European Pat. Off. .
0085985  8/1983  European Pat. Off. .
1404022  8/1975  United Kingdom .

OTHER PUBLICATIONS

C. W. Thornber, Quarterly Reviews, p. 563 (1978).
Durant et al., J. Med. Chem. 20:901–906 (1977).
Durant et al., Burgers Medicinal Chemistry (John Wiley 1981), fourth edition, Chapter 48, p. 520.
Beattie et al., J. Med. Chem. 20, p. 719 (1977).
Tilley et al., J. Med. Chem. 23, p. 1438 (1980).
Petersen et al., J. Med. Chem. 21, p. 773 (1978).

Primary Examiner—Mark L. Berch
Attorney, Agent, or Firm—Mark R. Daniel; Janice E. Williams; Alan D. Lourie

[57] ABSTRACT

This invention relates to cyanoguanidine derivatives that have utility in the treatment of congestive heart failure. A specific compound of this invention is 6-[4-($N^3$-methyl-$N^2$-cyanoguanidino)phenyl]-5-methyl-4,5-dihydro-3(2H)-pyridazinone.

27 Claims, No Drawings

6-(CYANOGUANIDINOPHENYL)PYRIDAZINONES AS CARDIAC STIMULANTS

The present invention relates to dihydropyridazinone derivatives and in particular to such compounds having a substituted phenyl group at the 6-position of the dihydropyridazinone ring. This invention further relates to processes for their preparation, intermediates in their preparation, their use as therapeutic agents and to pharmaceutical compositions containing them. The compounds of this invention are selective phosphodiesterase type III inhibitors and are of use in combatting such conditions wherein such inhibition is thought to be beneficial. Thus the compounds of this invention are positive inotropic agents and vasodilators and are therefore of value in combatting cardiovascular disease, in particular congestive heart failure. In addition the compounds of this invention inhibit platelet aggregation and therefore have an antithrombotic effect. Furthermore the compounds of this invention are bronchodilators and are therefore of use in combatting chronic obstructive lung diseases such as asthma and bronchitis. The major utility of the compounds of this invention is in the treatment of congestive heart failure, for such treatment the compounds have a very desirable profile of activity and duration.

Congestive heart failure is traditionally treated with cardiac glycosides, for example digoxin and digitoxin, and sympathomimetic agents. The glycosides have pronounced toxic effects with a low therapeutic index. The sympathomimetic agents generally do not have the desired profile of activity and are not orally effective. Amrinone is a marketed compound of interest that is reported to be an inotropic agent. This has an undesirable profile of side-effects when administered orally and development is being restricted to other modes of administration. Clearly there is a continuing need for orally active inotropic agents that have a good therapeutic profile.

Accordingly the present invention provides compounds of the formula (I):

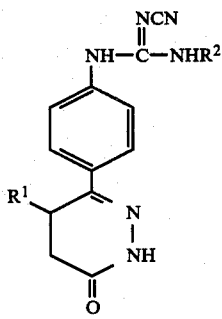

(I)

and pharmaceutically acceptable salts thereof, wherein $R^1$ is hydrogen or methyl and $R^2$ is hydrogen or $C_{1-4}$alkyl.

$R^1$ is hydrogen or methyl. Preferably $R^1$ is methyl, as such compounds give improved activity and duration of action.

$R^2$ is hydrogen or $C_{1-4}$alkyl, that is methyl, ethyl, n-propyl, isopropyl, n-butyl, isobutyl, sec-butyl and tert-butyl. Suitably $R^2$ is hydrogen, methyl, ethyl, n-propyl, isopropyl or n-butyl. Preferably $R^2$ is hydrogen, methyl or ethyl as such compounds give improved activity. In particular $R^2$ is methyl or ethyl and favourably is methyl.

Particular compounds of this invention are:
6-[4-($N^3$-methyl-$N^2$-cyanoguanidino)phenyl]-5-methyl-4,5-dihydro-3(2H)-pyridazinone,
6-[4-($N^3$-ethyl-$N^2$-cyanoguanidino)phenyl]-5-methyl-4,5-dihydro-3(2H)-pyridazinone,
6-[4-($N^3$-isopropyl-$N^2$-cyanoguanidino)phenyl]-5-methyl-4,5-dihydro-3(2H)-pyridazinone,
6-[4-($N^3$-butyl-$N^2$-cyanoguanidino)phenyl]-5-methyl-4,5-dihydro-3(2H)-pyridazinone, and
6-[4-($N^2$-cyanoguanidino)phenyl]-5-methyl-4,5-dihydro-3(2H)-pyridazinone.

Therefore in a favoured aspect of the present invention, preferred compounds are those of the formula (II):

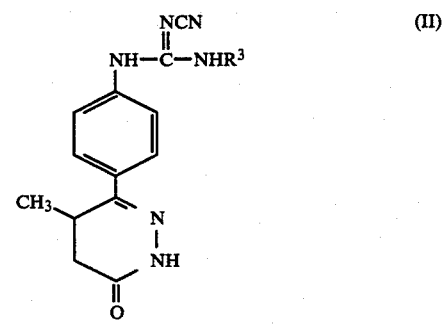

(II)

and pharmaceutically acceptable salts thereof, wherein $R^3$ is methyl or ethyl.

The compounds of the invention are depicted as dihydropyridazin-3(2H)-ones, but of course the present invention covers all tautomeric forms thereof, for example the dihydropyridazinol form and all the tautomeric forms of the —NH—C(=NCN)NHR$^2$ group. Furthermore the present invention covers all optical isomeric forms of the compounds of the formula (I).

Compounds of the formula (I) may form pharmaceutically acceptable salts with metal ions, such as alkali metals for example sodium and potassium, or alkaline earth metals for example calcium and magnesium.

In order to use a compound of the formula (I) or a pharmaceutically acceptable salt thereof for the treatment of humans and other mammals it is normally formulated in accordance with standard pharmaceutical practice as a pharmaceutical composition.

Compounds of formula (I) and their pharmaceutically acceptable salts may be administered in standard manner for the treatment of the indicated diseases, for example orally, parenterally, trans-dermally, rectally, via inhalation or via buccal administration.

Compounds of formula (I) and their pharmaceutically acceptable salts which are active when given orally or via buccal administration can be formulated as syrups, tablets, capsules and lozenges. A syrup formulation will generally consist of a suspension or solution of the compound or salt in a liquid carrier for example, ethanol, glycerine or water with a flavouring or colouring agent. Where the composition is in the form of a tablet, any pharmaceutical carrier routinely used for preparing solid formulations may be used. Examples of such carriers include magnesium stearate, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil, for example polyethylene glycol, polyvinylpyrrolidone, lecithin, arachis oil, or sesame oil.

A typical suppository formulation comprises a compound of formula (I) or a pharmaceutically acceptable salt thereof which is active when administered in this way, with a binding and/or lubricating agent, for example polymeric glycols, gelatins, cocoa-butter or other low melting vegetable waxes or fats.

Typical transdermal formulations comprise of a conventional aqueous or non-aqueous vehicle, for example a cream, ointment, lotion or paste or in the form of a medicated plaster, patch or membrane.

Typical compositions for inhalation are in the form of a solution, suspension or emulsion that may be administered in the form of an aerosol using a conventional propellant such as dichlorodifluoromethane or trichlorofluoromethane.

Preferably the composition is in unit dosage form, for example a tablet, capsule or metered aerosol dose, so that the patient may administer to himself a single dose.

Each dosage unit for oral administration contains suitably from 0.01 mg/Kg to 3 mg/Kg, and preferably from 0.05 mg/Kg to 1.5 mg/Kg, and each dosage unit for parenteral administration contains suitably from 0.001 mg/Kg to 1 mg/Kg, of a compound of formula (I) or a pharmaceutically acceptable salt thereof calculated as the free base.

The daily dosage regimen for oral administration is suitably about 0.01 mg/Kg to 12 mg/Kg, of a compound of formula (I) or a pharmaceutically acceptable salt thereof calculated as the free base. The daily dosage regimen for parenteral administration is suitably about 0.001 mg/Kg to 4 mg/Kg, for example about 0.01 mg/Kg to 1 mg/Kg, of a compound of the formula (I) or a pharmaceutically acceptable salt thereof calculated as the free base. The active ingredient may be administered from 1 to 4 times a day, sufficient to increase cardiac output. The compositions of the present invention have positive inotropic activity and vasodilator activity and are of use in the treatment of cardiovascular diseases which can be treated by compounds having either or both of these activities. One such disease condition is congestive heart failure. The compounds of the invention are also bronchodilators and are useful in chronic obstructive lung disease for example asthma and bronchitis. Such conditions can be treated by administration orally, rectally, parenterally or by inhalation. For administration by inhalation dosages are controlled by a valve and are conveniently in the range 0.1–5.0 mg of a compound of the formula (I) or a pharmaceutically acceptable salt thereof.

The compounds of this invention may be co-administered with other pharmaceutically active compounds, for example in combination, concurrently or sequentially. Conveniently the compounds of this invention and the other active compound or compounds are formulated in a pharmaceutical composition. Examples of compounds which may be included in pharmaceutical compositions with the compounds of the formula (I) are vasodilators for example hydralazine, angiotensin converting enzyme inhibitors for example captopril, anti-anginal agents for example isosorbide nitrate, glyceryl trinitrate and pentaerythritol tetranitrate, anti-arrhythmic agents for example quinidine, procainamide and lignocaine, cardioglycosides for example digoxin and digitoxin, calcium antagonists for example verapamil and nifedipine, diuretics such as thiazides and related compounds for example bendrofluazide, chlorothiazide, chlorothalidone, hydrochlorothiazide, and other diuretics for example frusemide and triamterene, and sedatives for example nitrazepam, flurazepam and diazepam.

In another aspect the present invention provides a process for the preparation of a compound of the formula (I) or pharmaceutically acceptable salt thereof, which process comprises:

(a) reacting a compound of the formula (III):

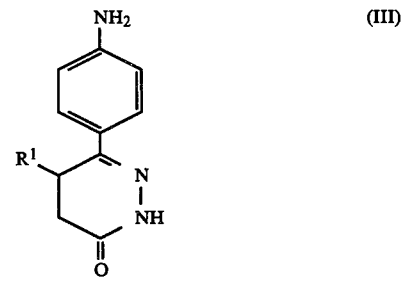

wherein $R^1$ is as hereinbefore defined, with a compound of the formula (IV):

wherein $L^1$ is a leaving group, and R is a group $-NHR^2$ wherein $R^2$ is as hereinbefore defined or R is a leaving group $L^2$; and thereafter if R is a leaving group $L^2$ reacting with an amine $NH_2R^2$ wherein $R^2$ is as hereinbefore defined; or (b) reacting a compound of the formula (V):

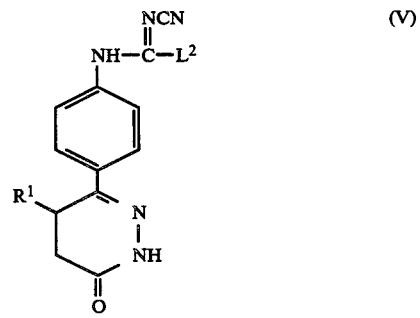

with an amine $NH_2R^2$, wherein $L^2$, $R^1$ and $R^2$ are as hereinbefore defined; or (c) reacting a compound of the formula (VI):

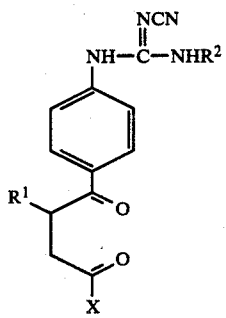

wherein $R^1$ and $R^2$ are as hereinbefore defined and X is a displaceable group, with hydrazine or a chemical equivalent thereof; or (d) reacting a compound of the formula (VII):

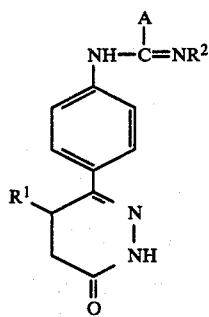

wherein $R^1$ and $R^2$ are as hereinbefore defined, and A is a displaceable group, with cyanamide or a heavy metal salt thereof;

(e) for compounds of the formula (I) wherein $R^2$ is hydrogen, reacting a compound of the formula (III) as hereinbefore defined with a salt of dicyanamide;
and thereafter optionally forming a pharmaceutically acceptable salt.

In the reaction between the compounds of the formulae (III) and (IV), R can be a group —$NHR^2$ so that a compound of the formula (I) is formed directly. In a preferred alternative R is a leaving group $L^2$ which may be the same as, or different to, the leaving group $L^1$. Suitably $L^1$ and $L^2$ are both benzylthio or $C_{1-6}$alkylthio, for example they are preferably both methylthio. Such a reaction is conveniently performed in a solvent such as pyridine at an elevated temperature for example reflux. Suitably also $L^1$ and $L^2$ are each selected from $C_{1-6}$alkoxy, phenoxy or benzyloxy, preferably both $L^1$ and $L^2$ are phenoxy. Such a reaction is conveniently performed in an aprotic organic solvent such as dimethylformamide, or a $C_{1-4}$alkanol for example ethanol, at an elevated temperature, for example between 50° C. and 150° C., preferably between 100°–130° C.

When $L^1$ and $L^2$ are leaving groups the reaction of the compounds of the formulae (III) and (IV) affords the compound of the formula (V). This can be isolated and reacted, or reacted in situ, with an amine: $R^2NH_2$. Suitably such a reaction can be performed in a $C_{1-4}$alkanol, for example ethanol, at an elevated temperature for example between 50° C. and reflux, that is about 79° C. for ethanol. Suitable and preferred leaving groups $L^2$ for formula (V) are the same as for formula (IV). Optionally the displacement of a leaving group $L^2$ can be performed in the presence of a salt of a heavy metal, in particular when $L^2$ is alkylthio. Suitably salts of heavy metals include salts of silver, mercury, cadmium or lead, preferably silver nitrate or mercuric chloride. In such cases the reaction is preferably performed in the presence of a base for example potassium carbonate.

The reaction between a compound of the formula (VI) and hydrazine or a chemical equivalent thereof is suitably performed at ambient or elevated temperature, for example 15° C.–120° C., preferably about 30° C.–80° C. or at reflux temperature of a suitable solvent. The reaction is conveniently performed in a solvent such as a $C_{1-4}$alkanol for example methanol, ethanol or n-propanol, or aqueous or glacial acetic acid. Suitably in the compounds of the formula (VI) X is hydroxy, $C_{1-6}$alkoxy, amino or $C_{1-6}$alkylamino.

In the reaction of a compound of the formula (VII) and cyanamide or a heavy metal salt thereof, suitably A is mercapto (—SH), i.e. tautomeric with a thiourea, and can be reacted with a heavy metal salt of cyanamide, for example, a lead, mercury or cadmium salt. Conveniently such reactions can be carried out in acetonitrile or dimethylformamide. In an alternative in the compounds of the formula (VII) A can be $C_{1-4}$alkylthio, $C_{1-4}$alkoxy, phenoxy or benzyloxy. Such compounds can be reacted with cyanamide in the presence of a strong base for example those having anions of weak nucleophilic character such as sodium hydride or potassium t-butoxide. Suitably the reaction is carried out in a solvent under anhydrous conditions and preferably at an elevated temperature for example 60° C.–120° C., conveniently at the reflux temperature of a $C_{1-4}$alkanol. When potassium t-butoxide is the strong base it is convenient to use t-butanol as solvent. Preferably A is $C_{1-4}$alkylthio.

The reaction of a compound of the formula (III) and a salt of dicyanamide is conveniently performed in aqueous acidic conditions, for example in a mixture of acetic acid and a mineral acid such as hydrochloric acid. The reaction is conveniently carried out at ambient temperature. Preferably the dicyanamide is in the form of the sodium salt.

The compounds of the formula (III) are known from Curran et al., J. Medicinal Chemistry, 17, p 273 (1974).

The compounds of the formula (VI) can be prepared by reacting a compound of the formula (VIII):

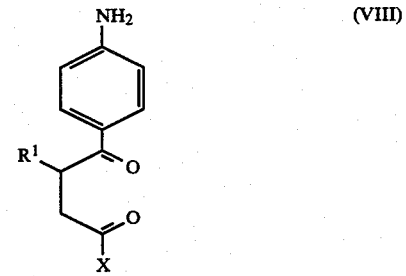

wherein $R^1$ and X are as hereinbefore defined, with a compound of the formula (IV) as hereinbefore defined; in an analogous manner to that described for reacting compounds of the formulae (III) and (IV). The compounds of the formula (VIII) are known, or preparable in conventional manner, from the above-mentioned J. Medicinal Chemistry reference.

The compounds of the formula (VII) are known from EP-A-No. 84250 or can be prepared in conventional manner.

The preparation of compounds of the formula (I) in general is summarised in the following scheme.

SCHEME

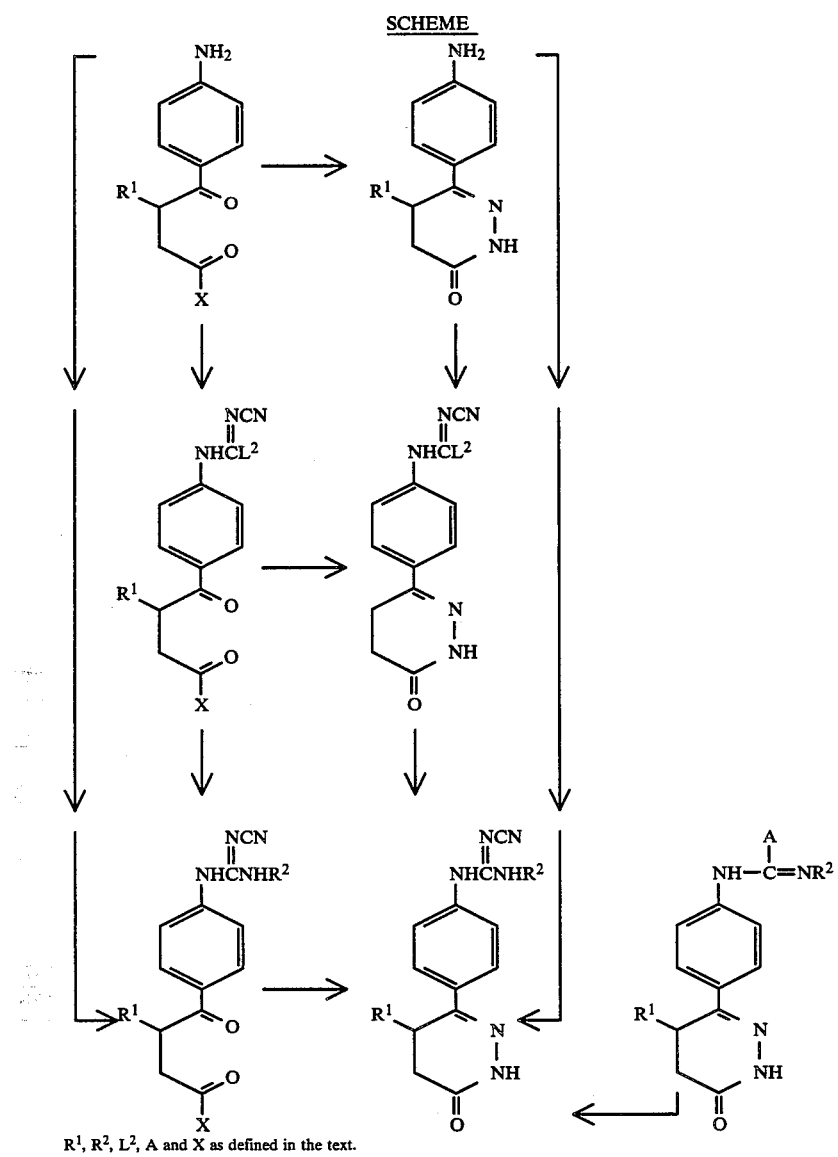

$R^1$, $R^2$, $L^2$, A and X as defined in the text.

The compounds of the formula (V) are primarily of interest as intermediates in the preparation of compounds of the formula (I). In addition, however, they are active compounds in their own right as phosphodiesterase inhibitors and in particular show positive inotropic and vasodilator activity.

Accordingly in a further aspect the present invention provides compounds of the formula (V) as hereinbefore defined and pharmaceutically acceptable salts thereof for use as therapeutic agents, in particular in the treatment of congestive heart failure.

Preferably in the compounds of the formula (V) $R^1$ is methyl.

$L^2$ in the compounds of the formula (V) is suitably $C_{1-6}$alkylthio for example methylthio, $C_{1-6}$alkoxy for example methoxy or ethoxy, phenoxy or benzyloxy. Preferably $L^2$ is methylthio or $C_{1-4}$alkoxy for example methoxy, ethoxy or propoxy. In particular $L^2$ is ethoxy.

The compounds of the formula (V) and pharmaceutically acceptable salts thereof can be formulated, used and tested as herein defined for the compounds of the formula (I).

The following biological test methods, data and Examples serve to illustrate this invention.
Cardiac Stimulant Activity—In vitro The compounds of formula (I) and their pharmaceutically acceptable salts are tested for cardiac stimulant activity following a procedure based on that of S. C. Verma and J. H. McNeill (J.Pharm & Exp. Therapeutics, 200, 352–362 (1977)). Guinea pigs (500–700 g) of either sex are sacrificed and the hearts are quickly removed and transferred to a dissecting dish containing oxygenated bathing fluid. While in the bathing medium, the right ventricle is cut into two strips. The strips are each suspended in a 50 ml bath containing Krebs Henseleit solution at 37° C., and the bath is bubbled with 95% oxygen and 5% carbon dioxide. The ventricular strips are electrically stimulated at a frequency of 1.0 Hz, at double the threshold voltage. A resting tension of 1.0 g is applied to the strips and the tension is kept constant by readjustment during an equilibration period of 60 minutes. The bathing fluid is frequently changed during this period. When a steady base line is obtained, a compound under test is added to the bathing fluid and a cumulative concentration response curve is plotted. The compounds for use in the present invention which were tested gave a 50% increase in the force of contraction of the ventricular strips at concentrations in the bathing fluid of less than $10^{-4}$ molar, thus showing that they have activity as positive inotropic agents.

In the above test method the compounds of the Examples gave the following data:

| Compound of Example | $EC_{50} \times 10^{-6}$ M |
|---|---|
| 1 | 1.4 |
| 3 | 1.4 |
| 4 | 0.8 |
| 5 | 8.5 |
| 6 | 1.4 |
| 8 | 40% at 31.6 |
| Amrinone | 15 |

Cardiac Stimulant Activity—In vivo (Anaesthetised Cats)

In anaesthetised cats pretreated with a ganglion blocker (mecamylamine or pempidine) and propranolol, the compounds of the Examples caused sustained increases in left ventricular dp/dt max (this is an index of left ventricular contractility) when administered intravenously. The dose to increase left ventricular dp/dt max by 50% is given as the $ED_{50}$.

| Compound of Example | $ED_{50}$ (micromol/kg) | Relative # Duration |
|---|---|---|
| 1 | 0.2 | *** |
| 3 | 0.2 | *** |
| 4 | 0.2 | ** |
| 5 | 0.31 | ** |
| 6 | 0.7 | *** |
| 8 | 1.6 | ** |
| Amrinone | 5.6 | * |

Relative duration was estimated in the anaesthetised cats following the i.v. administration
***long
**medium
*short Minimal changes in blood pressure or heart rate were observed.

Cardiac Stimulant Activity—In vivo (Conscious Dogs)

The compound of Example 1 increased left ventricular dp/dt max in conscious dogs after intravenous administration at doses below 0.1 mg/kg. Oral administration caused positive inotropic responses at doses of 0.25 mg/kg and below. These positive inotropic responses persisted for up to 9–12 hours without changes in blood pressure or heart rate. Therefore this compound is particularly beneficial with regard to 'force-rate' selectivity. In contrast amrinone is less active and is of shorter duration.

Vasodilator Activity:

The compound of Example 1 caused dose-dependent vasodilatation in anaesthetised rat hindquarters (autoperfused at constant blood pressure) over the dose range 1–10 μmol/Kg (i.v.). The dose to increase hindquarters blood flow by 50% was 4.6 μmol/Kg. A significant duration of activity was observed.

The compounds of Examples 3, 4, 5 and 8 were tested in autoperfused anaesthetised cat hindquarters (autoperfused at constant blood flow). The doses to decrease hindquarters perfusion pressure (vasodilatation) by 15% are given below:

| Compound of Example | |
|---|---|
| 3 | 44 μg/Kg |
| 4 | 82 μg/Kg |
| 5 | 130 μg/Kg |
| 8 | 1 mg/Kg |

Bronchodilatation—In vivo

Male guinea-pigs of the Dunkin Hartley strain (530 g±6 g) were anaesthetised with Sagatal (pentobarbital sodium) (90 mg/kg i.p.). Airway resistance was measured using a modification of the classical Konzett-Rossler technique (Versuchsanordnung zu Untersuchungen an der Bronchialmuskulatur. Naunyn-Schmiedebergs Arch. Exp. Path. Pharmak., 30: pp 121–145, (1940)). A dose of 2-pyridylethylamine which gave approximately 100% increase in airway resistance was selected for i.v. administration. Bolus doses of the compound of Example 1 were administered (i.v.) one minute before the 2-pyridylethylamine challenge.

The compound of Example 1 reduced the 2-pyridylethylamine-induced bronchoconstriction. The threshold dose for this compound was $3.16 \times 10^{-8}$ mol/kg. The dose of the compound of Example 1 which reduced the 2-pyridylethylamine bronchoconstriction by 50% ($ED_{50}$) was $3.9 \times 10^{-7}$ mol/kg, demonstrating in-vivo anti-bronchoconstrictor activity.

Platelet Aggregation Inhibition—In vitro

Plasma was prepared as follows. Blood from 6 normal healthy volunteers was mixed with 3.8% w/v trisodium citrate (9 parts blood: 1 part citrate). The samples were centrifuged at 150 g for 10 minutes and the supernatant platelet rich plasma (PRP) was removed. The platelet concentration in the PRP was adjusted to $300 \pm 50 \times 10^9/1$ platelets with autologous platelet poor plasma.

25 μl aliquots of a 40 μg/ml solution of the compound of Example 1 were incubated with 225 μl aliquots of PRP in a Payton Aggregometer for 3 minutes. Control solutions, one matched to the test solution with respect to solution pH and tonicity, and another of 0.9% w/v NaCl were also studied. After 3 minutes 25 μl aliquots of adenosine diphosphate solution at a concentration of 20 μm were added to each solution. The aggregation response was recorded until complete with a maximum of 3 minutes. The procedure was repeated using as different aggregation agents: 100 μg collagen; 100 μm adrenaline or 5 mg/ml arachidonic acid instead of adenosine diphosphate.

The aggregation responses induced by the different aggregation agents were measured for the platelets from each donor. The results were assessed by visual examination of the aggregation tracing produced by the Payton aggregometer and semi-quantitatively assessed by measurement of the light transmission 3 minutes after adding the inducing agent.

The compound of Example 1 at final concentrations of 5 μg/ml inhibited platelet aggregation induced by adenosine diphosphate, arachidonic acid, collagen or adrenaline solutions. Serial dilutions of this compound were prepared and tested for inhibition of adenosine diphosphate induced aggregation. Second wave aggregation was completely inhibited by the compound of Example 1 at 0.5 μg/ml and above.

The compounds of this invention show no overt signs of toxicity at doses up to approximately 100 times a predicted therapeutic dose when dosed orally to conscious dogs.

EXAMPLE 1

6-[4-($N^3$-Methyl-$N^2$-cyanoguanidino)phenyl]-5-methyl-4,5-dihydro-3(2H)-pyridazinone (i) A solution of 6-(4-aminophenyl)-5-methyl-4,5-dihydro-3(2H)-pyridazinone (2.0 g, 0.0098 mol) and diphenyl cyanoiminocarbonate (2.4 g, 0.01 mol), in anhydrous dimethylformamide (15 ml) was stirred at 115°–120° C. for 6 hours. Further diphenyl cyanoiminocarbonate (0.6 g, 0.0025 mol) was then added and the solution heated for a further 2 hours.

Evaporation of the solvent under reduced pressure gave a brown residue which was washed with boiling ethanol and then recrystallised from aqueous dimethylformamide to give 6-[4-[($N^2$-cyano)phenoxyformamidino]phenyl]-5-methyl-4,5-dihydro-3(2H)-pyridazinone, 1.5 g, m.p. 164°–5° C. This can also be recrystallised from acetonitrile.

(ii) A mixture of the above formamidine (1.5 g, 0.0043 mol) and a solution of methylamine (33% in ethanol; 50 ml) was stirred and heated under reflux for 3.5 hours. The solution was evaporated to a small volume under reduced pressure and the residue dissolved in hot ethanol. After charcoal treatment the solution was treated with water and allowed to cool to give the title compound (1.0 g), m.p. 264°–5° C.

EXAMPLE 2

6-[4-($N^3$-Methyl-$N^2$-cyanoguanidino)phenyl]-5-methyl-4,5-dihydro-3(2H)-pyridazinone (i) To 6-(4-aminophenyl)-5-methyl-4,5-dihydro-3(2H)-pyridazinone (4 g) in anhydrous pyridine (25 ml) was added dimethyl cyanodithioiminocarbonate (5.75 g) and the mixture was stirred under reflux for 3 hours. The reaction mixture was evaporated under reduced pressure to approximately half volume, diluted with ethanol and allowed to stand to afford a solid (3.85 g). The filtrate on standing and on trituration yielded further solid (1.42 g). The solids were combined and dissolved in boiling pyridine (60 ml) containing a little water. The solution was filtered and reduced in volume to give a slurry which was diluted with acetone and left to stand. This afforded crystals of 6-(4-(N-cyano-S-methylisothioureido)phenyl)-5-methyl-4,5-dihydro-3(2H)-pyridazinone, (4.02 g), m.p. 231°–2° C. (decomp).

(ii) 6-(4-(N-Cyano-S-methylisothioureido)phenyl)-5-methyl-4,5-dihydro-3(2H)-pyridazinone, (48 g) was added to a solution of methylamine (33% in ethanol; 600 ml) with stirring, and the mixture was heated under reflux for 2 hours. The reaction mixture was then allowed to cool and filtered to afford the title compound (32 g), which on recrystallisation from aqueous dimethylformamide gave the title compound, m.p. 270°–2° C. This was identical by thin layer chromatography and nuclear magnetic resonance spectroscopy to the product of Example 1.

EXAMPLE 3

6-[4-($N^3$-Ethyl-$N^2$-cyanoguanidino)phenyl]-5-methyl-4,5-dihydro-3(2H)-pyridazinone 6-[4-[($N^2$-Cyano)phenoxyformamidino]phenyl]-5-methyl-4,5-dihydro-3(2H)-pyridazinone (2.0 g) and a solution of ethylamine (33% in ethanol; 75 ml) were stirred and heated under reflux for 3 hours. Further ethylamine (33% in ethanol; 75 ml) was added and the mixture stirred under reflux for a further 3 hours. The mixture was evaporated under reduced pressure to give a brown oil. This was triturated under chloroform to give a cream solid (1.15 g) which was subjected to column chromatography on silica (chloroform as eluant) to afford the title compound (0.40 g), m.p. 208°–9° C.

EXAMPLE 4

6-[4-($N^3$-Isopropyl-$N^2$-cyanoguanidino)phenyl]-5-methyl-4,5-dihydro-3(2H)-pyridazinone Isopropylamine (7.4 ml) was added to 6-(4-($N^2$-cyano)phenoxyformamidino]phenyl)-5-methyl-4,5-dihydro-3(2H)-pyridazinone (1.5 g) in ethanol (100 ml) and the mixture was stirred under reflux for 4 hours (further isopropylamine (3 ml) added after 2 hours). The mixture was evaporated under reduced pressure to give a pale green solid. Trituration under ethanol gave a cream solid (0.94 g) which was subjected to flash column chromatography on silica (chloroform grading to chloroform:methanol 40:1) to give the title compound as a white solid (0.65 g), m.p. 255° C.

EXAMPLE 5

6-[4-($N^3$-Butyl-$N^2$-cyanoguanidino)phenyl]-5-methyl-4,5-dihydro-3(2H)-pyridazinone A mixture of n-butylamine (0.7 g) and 6-(4-($N^2$-cyanophenoxyformamidino)phenyl)-5-methyl-4,5-dihydro-3(2H)-pyridazinone (2.0 g) in ethanol (100 ml) was stirred under reflux for 4 hours. The mixture was evaporated under reduced pressure to yield a pale yellow oil, which on trituration with diethyl ether gave an off-white solid. This was subjected to flash column chromatography on silica (eluting with chloroform grading to chloroform:methanol 40:1) to afford the title compound as a white solid (0.75 g), m.p. 184°–6° C.

EXAMPLE 6

6-[4-($N^2$-Cyanoguanidino)phenyl]-5-methyl-4,5-dihydro-3(2H)-pyridazinone 6-(4-($N^2$-Cyanophenoxyformamidino)phenyl)-5-methyl-4,5-dihydro-3(2H)-pyridazinone (2.0 g) in ethanol (100 ml) was stirred under reflux for 3 hours whilst ammonia gas was bubbled through the solution. The reaction mixture was allowed to stand overnight and then evaporated under reduced pressure to yield a sticky solid which was treated with boiling ethanol, to give a white solid (1.1 g). Recrystallisation from methanol gave the title compound (0.8 g), m.p. 258°–60° C. (decomp).

EXAMPLE 7

6-[4-($N^2$-Cyanoguanidino)phenyl]-5-methyl-4,5-dihydro-3(2H)-pyridazinone

A solution of sodium dicyanamide (0.5 g) in water (20 ml) was added to a solution of 6-(4-aminophenyl)-5-methyl-4,5-dihydro-3(2H)-pyridazinone (1.0 g) in a mixture of aqueous acetic acid (20 ml) and 10M hydrochloric acid (0.5 ml). The resultant solution was stirred at room temperature for 3 days. A precipitate formed which was collected, washed with water and then with ethanol, and dried to give the title compound (0.33 g), thin layer chromatography and nuclear magnetic reso-

EXAMPLE 8

6-[4-(N³-Methyl-N²-cyanoguanidino)phenyl]-4,5-dihydro3(2H)-pyridazinone (i) 6-(4-Aminophenyl)-4,5-dihydro-3(2H)-pyridazinone (5.0 g) and diphenyl cyanoiminocarbonate (0.9 g), were stirred in anhydrous dimethylformamide (20 ml) for 4 hours at 120° C. The reaction mixture was cooled, filtered and evaporated under reduced pressure to give an oil. This oil was extracted into boiling ethanol (1 L) which was reduced in volume (to about 30 ml) and filtered to give 6-[4-[(N²-cyano)phenoxyformamidino]-phenyl]-4,5-dihydro-3(2H)-pyridazinone (3.5 g). Further extraction of the oil with boiling ethanol yielded further product (2.2 g).

(ii) A mixture of the above formamidine (3.2 g) and a solution of methylamine (33% in ethanol; 100 ml) was stirred and heated under reflux for 3 hours. The mixture was filtered whilst hot and the solid washed with ethanol and diethyl ether. Impurities were extracted from this solid on stirring in boiling ethanol. The solid was then dissolved in hot dimethylformamide, treated with charcoal, filtered through diatomaceous earth and the filtrate was evaporated to low volume (about 5 ml). This was then triturated with hot ethanol (100 ml) and filtered to afford the title compound (1.1 g), m.p. 267° C. (decomp).

EXAMPLE 9

6-[4-(N³-Methyl-N²-cyanoguanidino)phenyl]-4,5-dihydro-3(2H)-pyridazinone (i) Diphenyl cyanoiminocarbonate (2.5 g) in anhydrous dimethylformamide (10 ml) and ethyl 4-aminobenzoyl propionate (2.3 g) in dimethylformamide (10 ml) were mixed, stirred at 120° C. for 4 hours and allowed to stand at room temperature for 16 hours. The reaction mixture was evaporated under reduced pressure to small volume to deposit a solid. This solid was recrystallised from ethanol to give N¹-[4-(3-ethoxycarbonylpropionyl)phenyl]-(N²-cyano)phenoxyformamidine (1.4 g), m.p. 163°–5° C. (decomp).

(ii) This compound is reacted with excess of a solution of methylamine (33% in ethanol) with stirring and heating to give N¹-[4-(3-ethoxycarbonylpropionyl)-phenyl]-N³-methyl-N²-cyanoguanidine, which is reacted with hydrazine hydrate at an elevated temperature to give 6-[4-(N³-methyl-N²-cyanoguanidino)-phenyl]-4,5-dihydro-3(2H)-pyridazinone.

EXAMPLE 10

6-[4-((N²-Cyano)ethoxyformamidino)phenyl]-5-methyl-4,5-dihydro-3(2H)-pyridazinone 6-(4-Aminophenyl)-5-methyl-4,5-dihydro-3(2H)-pyridazinone and diethyl cyanoiminocarbonate in dimethylformamide are heated to give the title compound.

This compound is reacted with methylamine to give the compound of Example 1.

EXAMPLE 11

6-[4-(N³-Methyl-N²-cyanoguanidino)phenyl]-5-methyl-4,5-dihydro-3(2H)-pyridazinone To a solution of N-cyano-N¹-methyl-O-phenylisourea (0.175 g) in anhydrous pyridine (3 ml) was added 6-(4-aminophenyl)-5-methyl-4,5-dihydro-3(2H)-pyridazinone (0.2 g). The mixture was stirred at room temperature for 3 hours, stirred under reflux for 4 hours and allowed to cool overnight. This mixture was evaporated under reduced pressure to give a solid which was triturated with diethyl ether to remove phenol. Thin layer chromatography indicated the presence of unreacted starting-material and the title compound.

EXAMPLE 12

6-[4-(N³-Methyl-N²-cyanoguanidino)phenyl]-5-methyl-4,5-dihydro-3(2H)-pyridazinone Solutions of 6-(4-aminophenyl)-5-methyl-4,5-dihydro-3(2H)-pyridazinone and N-cyano-N,S-dimethylisothiourea under reflux conditions in pyridine and anisole, or under fusion conditions (165° C.), gave, as indicated by thin layer chromatography, unreacted starting-material and the title compound.

EXAMPLE 13

(+) and (−)-6-(4-Aminophenyl)-5-methyl-4,5-dihydro-3(2H)-pyridazinone

Racemic 6-(4-aminophenyl)-5-methyl-4,5-dihydro-3(2H)-pyridazinone (0.240 g) in acetonitrile (4 ml) was added to a column of ionically bound (R)-N-(3,5-dinitrobenzoyl phenyl)-glycine on 40 μm γ-aminopropyl silanized silica (300 g), packed at 1794 KPa (260 p.s.i.), and eluted with a mixture of dichloromethane/methanol (99.5:0.5) at 621 KPa (90 p.s.i.). Detection was by u.v. at 280 nm. A broad peak was obtained from which three fractions were collected. Each fraction gave approximately 0.08 g of material.

The first fraction to be eluted from the column was found to be the (−)-isomer, of approximately 90% enantiomeric enrichment. The second fraction to be eluted was found to be an approximately 50:50 mixture. The third fraction to be eluted was found to be the (+)-isomer of approximately 80–85% enantiomeric enrichment.

Enantiomeric purity was determined by an analytical column packed with the same chiral material as that of the preparative column; but covalently bound to 5 μm γ-aminopropyl silanized silica with u.v. detection.

A further chromatographic separation on the optically enriched enantiomers under the same conditions gave the (−)-isomer (0.050 g) in greater than 97% enantiomeric excess and the (+)-isomer (0.050 g) in approximately 90% enantiomeric enrichment; A further chromatographic separation of the latter material afforded the (+)-isomer (0.010 g) having greater than 93% enantiomeric excess.

The selected column elutions were evaporated, triturated with diethyl ether, filtered, and the resultant solids washed with diethyl ether and dried at 80° C. for 18 hours to give (−)-6-(4-aminophenyl)-5-methyl-4,5-dihydro-3(2H)-pyridazinone, m.p. 203°–4° C.; $[\alpha]_D^{25} = -399°$ [concentration 0.74% in Ethanol:-H₂O:HCl(conc) (17:2:1)]; and (+)-6-(4-aminophenyl)-5-methyl-4,5-dihydro-3(2H)-pyridazinone, m.p. 206°–8° C.; $[\alpha]_D^{25} = +376°$ [concentration 0.53% in Ethanol:-H₂O:HCl(conc) (17:2:1)]. These compounds gave nuclear magnetic resonance spectra consistent with the structure.

The products of Example 13 were tested for selectivity as inhibitors of the phosphodiesterases (PDE) isolated from guinea pig ventricle. Three forms of PDE were isolated by ion-exchange chromatography using the method of Thompson et al, Adv. Nucleotide Research, vol 10, p 69, Brooker et al (Eds), Raven Press, 1979.

In separate experiments with the (−)-isomer, the (+)-isomer and racemic material, following a 10 minutes pre-incubation of the test compound with Type (III) PDE, PDE activity was measured at 1 μm cyclic AMP for 10 minutes (using a modification of the method of Davis and Daly, Journal of Cyclic Nucleotide Research, vol 5, p 65, Raven Press, 1979). $IC_{50}$ values were obtained for inhibition of 'low Km' Type (III) PDE activity:

|  | $IC_{50}$ (μM) |
| --- | --- |
| (−)-isomer | 9.6 ± 3.4 |
| (+)-isomer | 207 ± 88 |
| racemate | 37 ± 12.9 |

In the in vitro test for inotropic activity on guinea pig ventricular strip the (−)-isomer gave an $EC_{50}$ value of $1.4 \times 10^{-6}$M and the (+)-isomer gave an $EC_{50}$ value of $11.3 \times 10^{-6}$M.

In the anaesthetised cat screen the (−)-isomer was more active than the (+)-isomer with respect to positive inotropism and vasodilatation.

EXAMPLE 14

(−)-6-[4-($N^3$-Methyl-$N^2$-cyanoguanidino)phenyl]-5-methyl-4,5-dihydro-3(2H)-pyridazinone (−)-6-(4-Aminophenyl)-5-methyl-4,5-dihydro-3(2H)-pyridazinone (0.240 g) was stirred with dimethyl cyanodithioiminocarbonate (0.38 g) in dry pyridine (4 ml) under reflux for 6 hours. The reaction mixture was then evaporated down to an oily solid under vacuum at 50° C. Diethyl ether (approx. 20 ml) was added to the reaction mixture and stirred until a solid was obtained. The solid was then filtered and thoroughly washed with diethyl ether (approx. 20 ml) to give the corresponding 6-(4-(N-cyano-S-methylisothioureido)phenyl)-5-methyl-4,5-dihydro-3(2H)-pyridazinone.

This was then heated for 3 hours with excess methylamine in ethanol (33%;20 ml). The reaction mixture was then absorbed on 40–60 μm silica (3.0 g); placed in a medium pressure system on 15–25 μm silica (48 g) at 1794 KPa (260 p.s.i.) and eluted with dichloromethane/methanol (20:1) at 1035 KPa (150 p.s.i.).

The selected column elutions were evaporated to give a solid which was triturated with diethyl ether, filtered and thoroughly washed with diethyl ether and dried at 80° C. for 16 hours to afford the title compound (0.249 g), m.p. 228° C; $[\alpha]_D^{25} = -384°$ (0.74% in dimethylformamide). The nuclear magnetic resonance spectrum was consistent with the structure.

Under the reaction conditions for Example 14, i.e. in pyridine under reflux, and separately in the presence of methylamine, the starting-material showed no racemisation.

In the phosphodiesterase inhibition test system (described above in Example 13), this (−)-isomer gave an $IC_{50}$ value of 1.7±1 μM. In the in vitro test for inotropic activity on guinea pig ventricular strip the (−)-isomer gave an $EC_{50}$ value of $0.71 \times 10^{-6}$M. In the anaesthetised rat hindquarters screen for vasodilator activity the dose to increase hindquarters blood flow by 50% was 2.4 μM/Kg. In the anaesthetised cat screen the (−)-isomer was more active than the corresponding (+)-isomer of Example 15 with respect to positive inotropism and vasodilatation.

EXAMPLE 15

(+)-6-[4-($N^3$-Methyl-$N^2$-cyanoguanidino)phenyl]-5-methyl-4,5-dihydro-3(2H)-pyridazinone In a manner similar to that of Example 14, (+)-6-(4-aminophenyl)-5-methyl-4,5-dihydro-3(2H)-pyridazinone (0.130 g) gave the corresponding 6-(4-(N-cyano-S-methylisothioureido)phenyl)-5-methyl-4,5-dihydro-3(2H)-pyridazinone. This was reacted with methylamine to give the title compound (0.138 g): m.p. 235° C.; $[\alpha]_D^{25} = 364°$ (0.65% in dimethylformamide).

In the phosphodiesterase inhibition test system (described above in Example 13), this (+)-isomer gave an $IC_{50}$ value of 11.3±5.4 μM. In the in vitro test for inotropic activity on guinea pig ventricular strip the (+)-isomer gave an $EC_{50}$ value of $4.3 \times 10^{-6}$M. In the anaesthetised rat hindquarters screen for vasodilator activity the dose to increase hindquarters blood flow by 50% was 8.6 μM/Kg.

EXAMPLE 16

A pharmaceutical composition for parenteral administration was prepared by dissolving the title compound of Example 1 (0.02 g) in polyethylene glycol 300 (25 ml) with heating. This solution was then diluted with water for injections E.P. (to 100 ml). The solution was then sterilised by filtration through a 0.22 micron membrane filter and sealed in sterile containers.

Compositions containing the compound of Example 1 (0.04 g) in polyethylene glycol 300 were prepared in analogous manner.

EXAMPLE 17

Pharmaceutical compositions for oral administration were prepared by combining the following:

|  | % w/w |  |  |
| --- | --- | --- | --- |
| 6-[4-($N^3$—Methyl-$N^2$—cyanoguanidino)phenyl]-4,5-dihydro-5-methyl-3(2H)—pyridazinone, 2% w/w Soya lecithin in soya bean oil | 0.5 | 3.0 | 7.14 |
|  | 90.45 | 88.2 | 84.41 |
| Hydrogenated vegetable shortening and beeswax | 9.05 | 8.8 | 8.45 |

The formulations were then filled into individual soft gelatin capsules.

What is claimed is:

1. A compound of the formula (I):

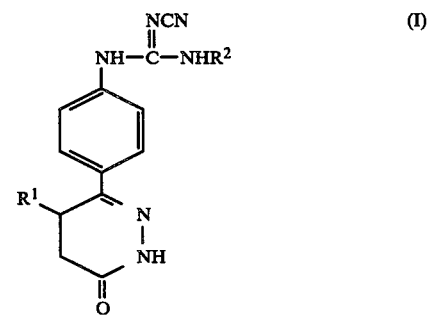

or a pharmaceutically acceptable salt thereof, wherein $R^1$ is hydrogen or methyl and $R^2$ is hydrogen or $C_{1-4}$alkyl.

2. A compound according to claim 1 wherein $R^1$ is methyl.

3. A compound according to claim 1 wherein $R^2$ is $C_{1-4}$alkyl.

4. A compound according to claim 2 wherein $R^2$ is $C_{1-4}$alkyl.

5. A compound according to claim 4 wherein $R^2$ is methyl or ethyl.

6. A compound according to claim 1 which is:
6-[4-($N^3$-methyl-$N^2$-cyanoguanidino)phenyl]-5-methyl-4,5-dihydro-3(2H)-pyridazinone,
6-[4-($N^3$-ethyl-$N^2$-cyanoguanidino)phenyl]-5-methyl-4,5-dihydro-3(2H)-pyridazinone,
6-[4-($N^3$-isopropyl-$N^2$-cyanoguanidino)phenyl]-5-methyl-4,5-dihydro-3(2H)-pyridazinone,
6-[4-($N^3$-butyl-$N^2$-cyanoguanidino)phenyl]-5-methyl-4,5-dihydro-3(2H)-pyridazinone,
6-[4-($N^2$-cyanoguanidino)phenyl]-5-methyl-4,5-dihydro-3(2H)-pyridazinone, or
6-[4-($N^3$-methyl-$N^2$-cyanoguanidino)phenyl]-4,5-dihydro-3(2H)-pyridazinone.

7. A compound according to claim 1 which is 6-[4-($N^3$-methyl-$N^2$-cyanoguanidino)phenyl]-5-methyl-4,5-dihydro-3(2H)-pyridazinone.

8. A compound according to claim 7 which is (−)-6-[4-($N^3$-methyl-$N^2$-cyanoguanidino)phenyl]-5-methyl-4,5-dihydro-3(2H)-pyridazinone.

9. A pharmaceutical composition which comprises a compound according to claim 1 and a pharmaceutically acceptable carrier.

10. A pharmaceutical composition which comprises a compound according to claim 7 and a pharmaceutically acceptable carrier.

11. A pharmaceutical composition which comprises a compound according to claim 8 and a pharmaceutically acceptable carrier.

12. A pharmaceutical composition according to claim 9 in unit dose form adapted for oral administration.

13. A pharmaceutical composition according to claim 10 in unit dose form adapted for oral administration.

14. A pharmaceutical composition according to claim 11 in unit dose form adapted for oral administration.

15. A method of treating congestive heart failure in a mammal comprising administering an effective amount of a composition of claim 9.

16. A method of treating congestive heart failure in a mammal comprising administering an effective amount of a compoistion of claim 10.

17. A method of treating congestive heart failure in a mammal comprising administering an effective amount of a composition of claim 11.

18. A method of stimulating cardiac activity in a mammal comprising administering an effective amount of a composition of claim 9.

19. A method of stimulating cardiac activity in a mammal comprising administering an effective amount of a composition of claim 10.

20. A method stimulating cardiac activity in a mammal comprising administering an effective amount of a composition of claim 11.

21. A method of effecting bronchodilatation in a mammal comprising administering an effective amount of a composition of claim 9.

22. A method of effecting bronchodilatation in a mammal comprising administering an effective amount of a composition of claim 10.

23. A method of effecting bronchodilatation in a mammal comprising administering an effective amount of a composition of claim 11.

24. A compound of the formula (V):

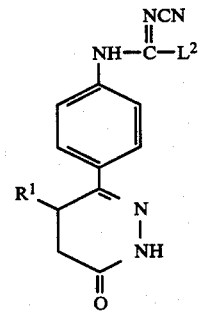

wherein $R^1$ is hydrogen or methyl and $L^2$ is selected from the group consisting of benzylthio, $C_{1-6}$alkylthio, $C_{1-6}$alkoxy, phenoxy and benzyloxy.

25. A compound according to claim 24 wherein $R^1$ is methyl and $L^2$ is phenoxy, $C_{1-6}$alkoxy or $C_{1-4}$alkylthio.

26. A compound according to claim 25 wherein $L^2$ is methylthio.

27. A compound according to claim 25 wherein $L^2$ is ethoxy.

* * * * *